(12) United States Patent
Vinayagamoorthy

(10) Patent No.: US 9,150,906 B2
(45) Date of Patent: Oct. 6, 2015

(54) DETERMINATION OF VARIANTS PRODUCED UPON REPLICATION OR TRANSCRIPTION OF NUCLEIC ACID SEQUENCES

(75) Inventor: Thuraiayah Vinayagamoorthy, Saskatoon (CA)

(73) Assignee: BIO-ID DIAGNOSTIC INC., Saskatchewan (CA)

( * ) Notice: Subject to any disclaimer, the term of this patent is extended or adjusted under 35 U.S.C. 154(b) by 0 days.

(21) Appl. No.: 11/475,921

(22) Filed: Jun. 28, 2006

(65) Prior Publication Data

US 2008/0003573 A1    Jan. 3, 2008

(51) Int. Cl.
*C12P 19/34* (2006.01)
*C12Q 1/68* (2006.01)

(52) U.S. Cl.
CPC ................................. *C12Q 1/6813* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis | |
| 4,683,202 A | 7/1987 | Mullis | |
| 4,775,619 A | 10/1988 | Urdea | |
| 4,851,331 A | 7/1989 | Vary | |
| 4,965,188 A | 10/1990 | Mullis | |
| 5,227,292 A * | 7/1993 | White et al. | 435/69.1 |
| 5,376,355 A | 12/1994 | Turteltaub | |
| 5,403,707 A | 4/1995 | Atwood | |
| 5,552,283 A | 9/1996 | Diamandis | |
| 5,582,989 A | 12/1996 | Caskey | |
| 5,622,824 A | 4/1997 | Koster | |
| 5,661,028 A | 8/1997 | Foote | |

(Continued)

FOREIGN PATENT DOCUMENTS

EP    0318341    5/1989
EP    0208418    12/1998

(Continued)

OTHER PUBLICATIONS

Wistow et al. (2002) Molecular Vision vol. 8:196-204.*

(Continued)

*Primary Examiner* — Suchira Pande
(74) *Attorney, Agent, or Firm* — Morrison & Foerster LLP

(57) ABSTRACT

A method of determining whether or not a nucleic acid having an expected sequence or one or more variants of the expected sequence are present in a sample containing nucleic acids after replication, transcription or editing (or other transformation) of a substrate nucleic acid. The method involves deciding an expected sequence likely to be formed in the sample upon the replication, transcription or editing of the substrate nucleic acid, and possible variants of the expected sequence, providing primer pairs for a polymerase chain reaction, reverse transcriptase polymerase chain reaction or ligase chain reaction, carrying out the polymerase chain reaction or reverse transcriptase polymerase chain reaction in one or more steps to form amplicons, and analyzing the amplicons to determining whether or not a nucleic acid having the expected sequence and/or variants are present in the sample. The primers of the primer pairs are designed to anneal to regions of the nucleic acid of the expected sequence and the variants, the regions being selected to reveal unambiguously the presence or absence in the sample of the nucleic acid of the expected sequence or the variants thereof according to the presence or absence of specific amplicons amplified by the primers.

6 Claims, 8 Drawing Sheets

(56) References Cited

U.S. PATENT DOCUMENTS

| | | | |
|---|---|---|---|
| 5,711,310 A | 1/1998 | Vinayagamoorthy | |
| 5,776,737 A | 7/1998 | Dunn | |
| 5,912,129 A | 6/1999 | Vinayagamoorthy | |
| 5,994,528 A | 11/1999 | Vinayagamoorthy | |
| 6,010,908 A * | 1/2000 | Gruenert et al. | 435/463 |
| 6,140,110 A | 10/2000 | Vinayagamoorthy | |
| 6,197,510 B1 | 3/2001 | Vinayagamoorthy | |
| 6,998,473 B1 * | 2/2006 | Crofts et al. | 536/23.5 |
| 7,691,614 B2 * | 4/2010 | Senapathy | 435/91.2 |
| 2003/0165868 A1 | 9/2003 | Lacroix | |
| 2004/0219565 A1 * | 11/2004 | Kauppinen et al. | 435/6 |
| 2007/0072212 A1 | 3/2007 | Vinayagamoorthy | |
| 2008/0118915 A1 | 5/2008 | Vinayagamoorthy | |

FOREIGN PATENT DOCUMENTS

| | | |
|---|---|---|
| WO | WO9104270 | 4/1991 |
| WO | WO9113993 | 9/1991 |
| WO | WO9119816 | 12/1991 |
| WO | WO9306243 | 4/1993 |
| WO | WO9410315 | 5/1994 |
| WO | WO9421822 | 9/1994 |
| WO | WO9511294 | 4/1995 |
| WO | WO9743441 | 11/1997 |
| WO | WO9826095 | 6/1998 |
| WO | WO9929900 | 6/1999 |
| WO | WO0020628 | 4/2000 |
| WO | WO2007095723 | 8/2007 |
| WO | PCT/CA2007/002333 | 8/2008 |

OTHER PUBLICATIONS

Marechal et al. (2001) Hum Genet 108:290-298.*
Johnson et al. (2003) Science vol. 302: pp. 2141-2144.*
Surono et al. (1999) Human Molecular Genetics vol. 8 No. 3 pp. 493-500.*
Kapranov et al. (2005) genome research vol. 15: 987-997.*
Hui et al. (1996) Blood vol. 88: 4021-4028.*
Fredriksson et al. (Feb. 22, 2007) Nucleic Acids Research vol. 35 No. 7 e 47 doi:10.1093/nar/gkm078.*
Shigemori et al. (2005) ) Nucleic Acids Research vol. 33 No. 14 e126 doi:10.1093/nar/gni111.*
Gene Structure (2010) p. 1-8.*
Ray et al. (2001) Molecular Human Reproduction vol. 7 No. 5 pp. 489-494.*
Dunnen and Beggs (May 1, 2006) Current Protocols in Human Genetics 9.3.1-9.3.22.*
Bourdon J.C., et al., p53 isoforms can regulate p53 transcriptional activity, Aug. 30, 2005 Genes and Development 19(18):2122-37.
Fitch J.M., et al., Analysis of transcriptional isoforms of collagen types IX, II, and I in the developing avian cornea by competitive polymerase chain reaction (Jan. 1995) Developmental Dynamics 202(1):42-53.
Orban Ti et al., Expression profiles of BRCA1 splice variants in asynchronous and in G1/S synchronized tumor cell lines (Jan. 12, 2001) Biochemical and Biophysical Research Communications, 280(1):32-38.
Cross N., Detection of BCR-ABL in hematological malignancies by RT-PCR (1996) Methods in Molecular Medicine, Molecular Diagnosis of Cancer pp. 25-36.
Ursula Ehmer, Arndt Vogel, Jan Karl Schütte, Britta Krone, Michael P. Manns and Christian P. Strassburg, Variation of Hepatic Glucuronidation: Novel Functional Polymorphisms of the UDP-Glucuronosyltransferase UGT1A4, Hepatology, Apr. 2004, pp. 970-977.
Yamakawa, Hisashi and Ohara, Osama, A DNA Cycle Sequencing Reaction That Minimizes Compressions on Automated Fluorescent Sequencers, *Nucleic Acid Research*, vol. 25, No. 6, pp. 1131-1312, 1997.
Kotera, J., Fujishige, K., Michibata, H., Yuasa, K., Kubo, A., Nakamura, Y., and Omori, K., Characterization and effects of methyl-2-(4-aminophenyl)-1, 2-dihydro-1-oxo-7-(2-pyridinylmethoxy)-4-(3,4,5-trimethoxyphenyl)-3-isoquinoline carboxylate sulfate (T-1032), a novel potent inhibitor of cGMP-binding cGMP-specific phosphodiesterase (PDE5), *Biochem.Pharmacol.*, Nov. 1, 2000:60(9):1331-41.
Schmittgen, T.D., Teske, S., Vessella, R.L., True, L.D., and Zakrajsek, B.A., Expression of prostate specific membrane antigen and three alternatively spliced variants of PSMA in prostate cancer patients, *Int J Cancer*, Nov. 1, 2003:107(2):323-9.
Martin, M.M., Willardson, B.M., Burton, G.F., White, C.R., McLaughlin, J.N., Bray, S.M., Ogilvie, J.W. Jr., and Elton, T.S., Human angiotensin II type 1 receptor isoforms encoded by messenger RNA splice variants are functionally distinct, *Mol. Endocrinol.*, Feb. 2001:15(2):281-93.
He, X., EE, P.L., Coon, J.S., and Beck, W.T., Alternative splicing of the multidrug resistance protein 1/ATP binding cassette transporter subfamily gene in ovarian cancer creates functional splice variants and is associated with increased expression of the splicing factors PTB and SRp20, *Clin. Cancer Research*, Jul. 15, 2004:10(14):4652-60.
Wistow, G., Bernstein, S.L., Wyatt, M.K., Ray, S., Behal, A., Touchman, J.W., Bouffard, G., Smith, D., and Peterson, K., Expressed sequence tag analysis of human retina for the NEIBank Project: retbindin, an abundant, novel retinal cDNA and alternative splicing of other retina-preferred gene transcripts, *Molecular Vision*, Jun. 15, 2002:8:196-204.
Wharton, J., et al., Antiproliferative effects of phosphodiesterase type 5 inhibition in human pulmonary artery cells, *American J. Respir Critt Care Med. Epub*, Apr. 7, 2005:Jul. 1, 2005:172(1):105-13.
Li et al., "Direct electrophoretic detection of the allelic states of single DNA molecules in human sperm by using the polymerase chain reaction" Proc. Natl. Acad. Sci USA vol. 87, pp. 4580-4584, 1990.
Rawn, "Biochemistry" pp. 666, 708, Carolina Biological Supply, North Carolina 1989.
S.C. Roemer et al., Simultaneous Bi-Directional Cycle Sequencing, LI-COR Virtual Poster Session [on-line], Sep. 1997, retrieed on Sep. 4, 1998, from Internet.
D.L. Steffens et al., Multiplex Amplification of Human STR Loci using Infrared Fluorescence Detection, LI-COR Virtual Poster Session [on-line], Feb. 1997.
Visible Genetics, Inc., Application Note, HiV Genotyping using the OpenGene Automated DNA Sequencing System, Jan. 16, 1998.
Visible Genetics, Inc., Application Note, p53 Mutation Detection using the OpenGene Automated DNA Sequencing System, May 3, 1998.
Jones, Leslie B. et al.: "Octamer-primed cycle sequencing using dye-terminator, chemistry" Nucleic Acids Research, vol. 26, No. 11, 1998, pp. 2824-2426, XP002131455.
Horton, Joseph H.: "Optimized Conditions for Cycle Sequencing of PCR Products" PCR Methods and Applications, vol. 3, 1994, pp. 359-360, XP002131456.
White, Michael J. et al.: "Concatemer Chain Reaction: A Tag DNA Polymerase-Mediated Mechanism for Generating Long Tandemly Repetitive DNA Sequences" Analytical Biochemistry, US, Academic Press, San Diego, CA, vol. 199, No. 2, Dec. 1, 1991, pp. 184-190, XP000236491.
Kretz, Keith et al.: "Cycle Sequencing" PCR Methods & Applications, US, Cold Spring Harbor Laboratory Press, vol. 3, No. 5, Apr. 1, 1994, pp. S107-S112, XP000606764.
Sanger, F. et al.: "DNA Sequencing with Chain-Terminating Inhibitors" Proceedings of the National Academy of Sciences of the USA, US, New York, NY, vol. 74, No. 12, Dec. 1, 1977, pp. 5463-5467, XP000603873.
Verdin et al., Use of an internal control in a nested-PCR assay for Mycoplasma hyopneumoniae detection and quantification in tracheobronchiolar washings from pigs, Molecular and Cellular Probes (2000) 14, 365-372.
Reiter, et al, Human Meiotic Recombination Products Revealed by Sequencing a Hotspot for Homologous Strand Exchange in Multiple HNPP Deletion Patients, Am. J. Hum. Genet. 62:1023-1033, 1998.

(56) References Cited

OTHER PUBLICATIONS

Yang et al., Hypersensitive PCR, ancient human mtDNA, and contamination, Human Biology, vol. 75, pp. 355-364, 2003, pp. printed as 1-6.
Van Doornum et al., 2003, Diagnosing herpes virus infections by real time amplification and rapid culture,Journal of Clinical Microbiology, vol. 41, pp. 576-580.
Akduman et al.,Evaluation of a strand displacement amplification assay (BD ProbeTecSDA) for detection of Neisseria gonorrhea in urine specimens,(2002) Journal of Clinical Microbiology, vol. 40, pp. 281-283.
Roth et al., Feasibility and efficacy of routine PCR screening of blood donations for hepatitis C virus, hepatitis B virus, and HIV-1 in a blood-bank setting,(1999) Lancet, vol. 353 (9150), pp. 359-363.
Betsou et al.,Construction and evaluation of internal control Nucleic Acids for PCR amplifiation of Chlamydia trachomatis Nucleic Acids from urine samples, (2003) Journal of Clinical Microbiology, vol. 41, pp. 1274-1276.
Dingle et al., Stable and noncompetitive RNA internal control for routine clinical diagnostic reverse transcription-PCR, (2004) Journal of Clinical Microbiology, vol. 42, pp. 1003-1011.
Gonzalez et al., Multiple displacement amplification as a pre-polymerase chain reaction (pre-PCR) to process difficult to amplify samples and low copy number sequences from natural environments, (2005) Environ Microbiol., vol. 7, No. 7, p. 1024-1028.
Abu Al-Soud and Radstrom, Effects of amplification facilitators on diagnostic PCR in the presence of blood, feces, and meat, (2000) Journal of Clinical Microbiology, vol. 38, No. 12, pp. 4463-4470.
Vinayagamoorthy et al., 2003, Nucleotide sequence based multi-target identification, MultiGEN, Journal of Clinical Microbiology, pp. 3284-3292.
van Rooijen et al., Structural Requirements of Oleosin Domains for Subcellular Targeting to the Oil Body, Plant Physiol. (1995) 109:1353-1, 361.
Sullivan et al., Identification of human remains by amplification and automated sequencing of mitochondrial DNA, Int J Ieg Med (1992) 105:83-86.
Cone et al., Coamplified Positive Control Detects Inhibition of Polymerase Chain Reactions, Journal of Clinical Microbiology, Dec. 1992, p. 3185-3189, vol. 30, No. 12.
Molecular Typing of West Nile Virus, Dengue, and St. Louis Encephalitis Using Mutiplex Sequencing; Journal of Molecular Diagnostics; Moorthy, et al.; vol. 7, No. 2, May 2005.
DNA Sequence-Based High-Throughout Microbial Identification Using Multiplex Sequencing; Moorthy; American Biotechnology Laboratory, Dec. 2003.
Detection of Giardia Lamblia and Cryptosporidium Parvum in Water Samples Using Multiplex Sequencing Technology; Moorthy; American Laboratory, May 2004.
Rational Drug Design Based on Splice Variants; Moorthy; GEN vol. 24, No. 9, May 1, 2004.
Polymicrobial Disease Conference Chart: Identification of West Nile and Other Flaviviruses Using Multiplex Sequencing (MultiGEN), Oct. 19-23, 2003, Lake Tahoe.
Identifying MRSA with Multiplex Sequencing; Moorthy, et al.; GEN vol. 28, No. 6, Mar. 15, 2008.
Molecular cloning, sequencing, and analysis of the cDNA for rabbit muscle glycogen debranching enzyme, Vinayagamoorthy, et al. Archives of Biochemistry and Biophysics 1993 vol. 306 No. 1 pp. 232-239.
Molecular control of melanogenesis in malignant melanoma: functional assessment of tyrosinase and lamp gene families by UV exposure and gene co-transfection, and cloning of a cDNA encoding calnexin, a possible melanogenesis "chaperone", Vinayagamoorthy, et al. J Dermatol Nov. 1994; 21(11):894-906.
Novel type of plasmid-borne resistance to trimethoprim, Vinayagamoorthy, et al. Antimicrob Agents Chemother Jan. 1987; 31(1):60-66.
Identification of a cDNA coding for a Ca(2+)-binding phosphoprotein (p90), calnexin, on melanosomes in normal and malignant human melanocytes, Vinayagamoorthy et al. Exp Cell Res Dec. 1993; 209(2):288-300.
Characterization of melanosome-associated proteins by establishment of monoclonal antibodies and immunoscreening of a melanoma cDNA library through an anti-melanosome antibody, Vinayagamoorthy et al. Melanoma Res. Oct. 1993;3(5):331-6.
Research Report, A rapid non-selective method to generate quadromas by microelectrofusion. Vinayagamoorthy, et al. doi:10.1016/0022-1759(95)00160-C.
cDNA-based functional domains of a calnexin-like melanosomal protein, p90. Vinayagamoorthy et al. Melanoma Res. Aug. 1993;3(4):263-9.
Stress Relief Protein Modulation by Calnexin. Vinayagamoorthy et al. Annals of the New York Academy of Sciences, 1996.
Simultaneous genotyping of sexually transmitted bacterial pathogens using MultiGEN technology. Vinayagamoorthy et al. International Society for Sexually Transmitted Diseases, Congress (2003) Ottawa Canada.
Incidence of pGS01 and pGS04 type sulphonamide resistance genes among clinical isolates collected from hospitals in Sri Lanka. Vinayagamoorthy et al. Singapore Med J. Aug. 1986;27(4):312-6.
Identification of Food Pathogens Using Multiple Nucleotide Based Signature Sequences. Presentation apart of PS 6C: Biotechnology Applications. Vinayagamoorthy et al. Friday, Jul. 18, 2003.
Identification of the Severe Acute Respiratory Syndrome Coronavirus by Simultaneous Multigene DNA Sequencing. Vinayagamoorthy et al. Journal of Clinical Microbiology, Jul. 2004, p. 3291-3294, vol. 42, No. 7.
24 hour urine composition of Sri Lankan adults and their response to 100mg dihydrochlorothiazide. Vinayagamoorthy et al. Ann Clin Biochem Jul. 1980;17(4):212-3.
Mobilization of antibiotic resistance genes among farm animals and human hosts in a developing country (Sri Lanka). Vinayagamoorthy et al. Singapore Medical Journal 1987 vol. 28 No. 2 pp. 134-139.
R-plasmid-mediated antibiotic resistance genes among clinical isolates, "normal healthy" adults and a drinking water source in a developing country. Vinayagamoorthy et al. Asian Medical Journal vol. 29, No. 1, pp. 50-68 1986.
"Dual asymetric PCR: one-step construction of synthetic genes" Sandhu, G.S., et al. BioTechnics vol. 12, No. 1, Jan. 1992 pp. 14-16.
Gene synthesis and expression in E.coli for PMP, a human matrix metalloproteinase Ye, Q-Z, et al. Biochemical and Biophysical Research Communications vol. 186, Jul. 15, 1992, Duuth, Minnesota US.
"PCR Protocols" Innis et al., 1989 Academic Press, San Diego UP XP002098377 pp. 39-45.
"Improved Double-Stranded DNA Sequencing Using the Linear Polymerase Chain Reaction" Murray, Vincent Nucleic Acids Research vol. 17, No. 21 Nov. 1989, p. 8889 XP000371763.
"Automated Cycle Sequencing with Taquenase TM: Protocols for Internal Labeling, Dye Primer and "DoubleX" Simultaneous Sequencing" Voss et al., Biotechnics, vol. 23, No. 2, Aug. 1997, pp. 312-318, XP000698417.
"Cycle Sequencing Using Degenerate Primers Containing Inosines" Biotechnics, vol. 15, No. 1, Jul. 1, 1993, pp. 82, 84, 88-89, XP000385833.
"Point Mutation Analysis in a Mammalian Gene: Rapid Preparation of Total RNA, PCR Amplification of CDNA, and Tag Sequencing by a Novelmethod" Biotechnics, vol. 7, No. 5, May 1, 1989, pp. 494-496, 498/499, XP000406164.
"The Use of a Modified Taq DNA Polymerase for Thermal Cycle Sequencing of Double Strand Plasmid DNA Templates" Spurgeon, S. et al.,Human Genome II. Int'l Conference, Oct. 22, 1990, San Diego, CA.
"Molecular Cloning, A Laboratory Manual" Maniatis, T. et al., published 1982 by McGraw-Hill (NY), see pp. 133, 134 and 143.
"Synthesis of 3-(triethylstannyl) propanioc acid: an organotin mass label for DNA" Sloop et al., Bioconjugate Chemistry. 1993, vol. 4, pp. 406-409.
"Applications of mass spectrometry to DNA sequencing" Jacobsen et al., GATA. 1991, vol. 8, No. 8, pp. 223-229.

(56) References Cited

OTHER PUBLICATIONS

"Nucleic Acids: Overview and analytical strategies in: Mass Spectrometry in Biomolecular sceinces." Edited by R.M. Capriolo et al. Netherlands: Kluwer Academic Publishers, 1996, p. 351-379.

"Dual analyte immunoassay for proteins using releasable metal ions as labels (Albumin, immunoglobulin G)." Hayes et al., Dissertation Abstracts International. 1992, vol. 53, No. 9B, p. 4624.

"Covalent modification with concomitant inactivation of the cAMP dependent protein kinase by affinity labels containing only 1-amino acids" Salerno, et al., J. biol. Chem. 1993, vol. 268, No. 18, pp. 13043-13049.

"In Vivo Molecular and Cellular Imaging With Quantum Dots" Gao et al., Current Opinion in Biotechnology, 2005, 16:63-72.

"Luminescent Quantum Dots for Mutilplexed Biological Detection and Imaging" Chan et al. Current Opinion in Biotechnology, 2002, 13: 40-46.

"Engineered Nanomaterials for Biophotonic Applications: Improving Sensing, Imaging, and Therapeutics" West et al., Annual Review of Biomedical Engineering 2003; 5:285-92.

"Quantum Dots and Other Nanoparticles: What Can They Offer to Drug Discovery" Ozkan Drug Discovery Today, 2004, vol. 9, No. 24, 1065-1071.

"Multiple promoters direct the tissue-specific expression of novel N-terminal variant human vitamin D receptor gene transcripts" Crofts et al., Proc. Natl. Acad. Sci. USA Sep. 1998 95:10529-10534.

Non Final Office Action, U.S. Pat. No. 6,197,510, Mail Date Nov. 26, 1999.

* cited by examiner

DETERMINATION OF VARIANTS PRODUCED UPON REPLICATION OR TRANSCRIPTION OF NUCLEIC ACID SEQUENCES

BACKGROUND OF THE INVENTION

1. Field of the Invention

This invention relates to means for determining variants of an expected nucleic acid sequence in the population formed when a substrate nucleic acid sequence is replicated, transcribed, edited, or transformed in similar ways. More particularly, the invention relates to the determination of the formation of expected sequences or variants upon such transformations to establish a better understanding and utilization of the role of such variants in genetic processes.

2. Background Art

All life forms have specific genomes that are based either on DNA or RNA (referred to collectively herein as nucleic acids). During cell processing, nucleic acids derived from the genome or other sources are frequently and routinely copied (replicated), transcribed, edited (in the case of eukaryotic organisms), and eventually translated into proteins. During such processing, there is normally an "expected" nucleic acid sequence that results from "normal" replication, transcription or editing, but frequently one or more variants of the expected sequence are formed either in addition to the expected sequence or in place of it. The formation of such variants can result from "errors" in the replication, transcription or editing processes, or may possibly result from normal cell processes, e.g. when genes overlap.

Knowledge of the formation of one or more variants of an expected sequence when nucleic acid transformations take place can provide useful information for scientists in various fields. For example, the formation of sequence variants may be indicative of disease in a particular individual or may help to explain a particular cellular process.

For example, in higher life forms (based on eukaryotic cells), including humans, the primary RNA transcript formed directly from a genetic DNA sequence undergoes editing by the cell before it is used as a template for protein formation (translation). During this process, non-coding regions of the gene (introns) are removed and coding regions (exons) are spliced together to form a functional mRNA template used for protein synthesis. Often, in nature, this editing process leads to the formation of different versions of mRNA (often referred to as "splice variants"). These different versions or variants may differ in the number and/or order of the exons incorporated into the mRNA, as well as the variation of nucleotides across the junction or splice points of adjacent exons.

It is estimated that more than 70% of gene expression events encounter splice variations, thus resulting in variations in expressed proteins, which undermines the established concept that one gene leads to only one version of the protein. The presence or level of specific splice variants may be the cause or an indicator of a disease, disorder, pathological condition or normal condition. Understanding the distribution of splice variants in various tissues is extremely important for understanding the physiological function of genes and for targeting pharmaceuticals in drug discovery, drug evaluation, as well as for diagnostic purposes.

The formation of variants in this way is not limited to the translation of DNA to mRNA in eukaryotic cells. Even in prokaryotic cells (where there are no introns and thus no editing of RNA transcripts), there may be minor variations (mutations) in some of the transcripts. Moreover, during cell division in both prokaryotic and eukaryotic cells, DNA to DNA copies are made, involving a number of enzymes (e.g. RNA primase, DNA polymerase, exonuclease, ligase, etc.). Although these steps have built-in proof-reading mechanisms, such replication may result in variations in the copies of DNA formed leading to various abnormalities or diseases (Ref. 1, see References at the end of this disclosure).

A common way of determining the transcription products of cells of a tissue is to employ a DNA micro-array (often called a "gene chip"). In this method, short probes (each representing a gene) are printed on and secured to a slide or chip. The cDNA of the tested tissue, fluorescently labeled, is hybridized to the micro-array. The level of the resulting signal corresponds to the relative expression level of the associated nucleic segment in the population. However, such micro-arrays do not account for the variants among the population formed that carry such nucleic acid segments. Hence it is not the presence or absence of a nucleic acid segment that is important, but to determine and characterize the nucleic sequence species that carry those segments, e.g. if there is a nucleic segment (for example, an exon) that determines a drug binding site on the resultant protein, it is essential to know whether that exon is carried by a specific mRNA so that there will be proper folding of the protein resulting in specific protein structure conducive for binding of the drug.

In the recent past, computational modeling has been adopted as an alternative method for predicting protein structure, which is based on the amino acid sequences (primary structures) of proteins. Technical limitations of determining an amino acid sequence directly from the protein have made it necessary to predict the amino acid sequence from the nucleotide sequence of the mRNA template. The existence of splice variants formed during gene expression interferes with such predictions and has created two main problems for accurate prediction of protein structures: (a) exon composition in various mRNA transcripts formed (b) errors in splicing itself at the exon/exon junction of mRNA templates.

Presently, there is no method available to accurately determine all of the different transcripts that may be simultaneously expressed from a gene.

A method of determining all the sequence variants resulting from nucleic acid transformations would therefore be of practical significance.

SUMMARY OF THE INVENTION

An exemplary embodiment of the present invention provides a method of determining whether or not a nucleic acid having an expected sequence or one or more variant nucleic acids having a variant of the expected sequence is or are present in a sample containing nucleic acids after replication, transcription or editing of a substrate nucleic acid, which method comprises: deciding an expected sequence likely to be formed in the sample upon the replication, transcription or editing of the substrate nucleic acid, and possible variants of the expected sequence; providing at least one primer pair for a nucleic acid amplification step (e.g. polymerase chain reaction, reverse transcriptase polymerase chain reaction or ligase chain reaction), carrying out the amplification step to form one or more amplicons, and analyzing the one or more amplicons to determining whether or not a nucleic acid having the expected sequence or one or more variants is or are present in the sample, wherein primers of the at least one primer pair are designed to anneal to regions of the nucleic acid of the expected sequence and the one or more variant nucleic acid sequences, the regions being selected to reveal unambiguously the presence or absence in the sample of the nucleic acid of the expected sequence or the one or more variants thereof according to the presence or absence of amplicons amplified by the primers.

In most cases, the nucleic acid of expected sequence is known or can be readily determined, e.g. the sequence of DNA produced by replication (the sequence of the replicated DNA should be the same as the substrate DNA), or the mRNA transcribed from a known gene. Also, it is normally relatively easy to determine expected or suspected variants. For example, when exons of a gene are converted to mRNA, it can be expected that one or more of the exons may be missing, or the exons are aligned in a different order than the one expected. Further, when DNA containing a region of interest (e.g. a putative drug binding site in an eventual protein) is replicated or transcribed, a replicate or transcript lacking the region of interest may be suspected. The invention may be employed when there is an expected sequence and at least one expected or suspected variant of interest that may be formed. Primer sets can then be designed to reveal the presence or absence of such expected sequence and variant(s) in an unambiguous way (according to amplicons amplified by the primer sets) all in one PCR or RT-PCR procedure or in a sequence of two or more such procedures. Once the presence of at least one variant has been established in this way, the precise sequence of a region of interest (e.g. an exon:exon junction or a putative drug binding site) may be established, if desired, by cycle sequencing of such a region.

Procedures for designing and producing primers that anneal to short stretches of a known sequence are an integral part of the PCR and RT-PCR procedures and within the expected skill of persons knowledgeable in the art. When the substrate sequence is known, or at least the part that is relevant to the determination, the design of the primers involves identifying a suitable short stretch of the known sequence where amplification should begin and end, thereby generating suitable amplicons that give an unambiguous indication of the sample sequence, and creating a short stretch of complementary DNA that will anneal to the selected stretch of the sample DNA. Ideally, one primer set is designed for each of the expected sequence and all of the possible variants of interest, there being at least one variant of interest as well as the expected sequence.

Another exemplary embodiment of the invention provides a method of determining whether or not a nucleic acid having an expected sequence is present in a sample after linking together of at least two nucleic acid sequence units capable of forming the nucleic acid of the expected sequence, and whether at least one nucleic acid having a variants of the expected sequence is formed, which method comprises providing at least one pair of polymerase chain reaction primers designed to amplify a region of the nucleic acid of the expected sequence, the region crossing at least one junction between adjacent sequence units of the expected sequence, carrying out polymerase chain reaction or reverse transcriptase polymerase chain reaction on the sample employing the primers to permit amplification of the region, thereby forming an amplification product, carrying out an analysis of the amplification product to establish sizes of one or more amplicons present in the amplification product, and using information from the analysis to determine if a nucleic acid of the expected sequence was present in the sample and if one or more nucleic acids having variants of the expected sequence was or were formed during the linking together of the sequence units by omission of one or more of the sequence units or by variation of an expected order of assembly of the sequence units.

Yet another exemplary embodiment of the invention provides a method of determining a presence or absence of variants in a sample produced during the formation of nucleic acids upon linking of a plurality of known sequence units, which method comprises: providing a plurality of primer pairs adapted to amplify specific nucleic acid sequences during polymerase chain reactions or reverse transcriptase polymerase chain reaction, each of the plurality of primer pairs being designed to amplify partial sequences of two of the known sequence units, there being sufficient primer pairs of different design to provide amplified sequences containing partial sequences of all the known sequence units; carrying out polymerase chain reaction or reverse transcriptase polymerase chain reaction on the sample using the plurality of primer pairs simultaneously to produce a reaction mixture containing amplified nucleic acids of different lengths; establishing the lengths of the amplified nucleic acids; and determining the variants present in the sample based the lengths of the amplified nucleic acids.

A still further exemplary embodiment of the invention provides a method of determining an exact sequence of bases adjacent to a junction of two nucleic acid sequence units in a sample nucleic acid formed by linking of the sequence units, thereby to establish a presence or absence of variants of an expected sequence at the junction, which method comprises isolating and amplifying a region of the sample nucleic acid crossing the junction and including bases on each side of the junction, and subjecting the isolated region to cycle sequencing to determine an exact sequence of bases thereof.

In the context of the present invention, the term "sequence unit" means any nucleic acid sequence that is manipulated as a whole during the formation of a new nucleic acid sequence, e.g. by splicing together two or more such units obtained from a precursor sequence, such as a eukaryotic gene sequence. Thus, the exons of a eukaryotic gene are examples of sequence units when they are transcribed to RNA and spliced together to form mRNA during protein synthesis. It is when such units are joined, linked or spliced by natural or artificial processes that splice variants may be formed, e.g. by loss of one or more entire units, misalignment of the units compared to the expected alignment, and variation of bases at the junction of the units.

Also, as used herein, the term polymerase chain reaction (PCR) may include reverse transcription polymerase chain reaction (RT-PCR) carried out on an mRNA substrate, when the context makes this apparent.

The term "amplicon" as used herein means a molecule or collection of molecules (population) obtained by amplifying a particular nucleic acid sequence by PCR or RT-PCR.

Potential splice variant targets that may be investigated by the methods of the present invention include (but are not limited to) the following:
 1. Soluble Proteins:
    a. Lipitor® (Anticholesterol drug) target protein-3-hydroxy-3-methylglutaryl-coenzyme A (HMG-CoA)
    b. Viagra®—Phosphodiesterase type 5 (PDE 5)
       Splice variant has been reported (Ref. 2)
 2. Membrane Proteins:
    a. Prostrate cancer receptor—Prostrate specific membrane antigen
       Splice variant has been reported (Ref. 3)
    b. Human Angiotension II type receptor
       Splice variant has been reported (Ref. 4)
    c. ATP-binding cassette transporter A1, ABCA1
       Splice variant has been reported (Ref. 5)
    d. Human Usher syndrome harmonin
       Splice variant has been reported (Ref. 6)

e. HIV receptors CD 46, CD 4, CD 8
f. The human constitutive androstane receptor (hCAR; NR1I3
   Splice variant has been reported
g. Serum response factor (SRF)
   Splice variant has been reported
h. Sodium-Proton pump receptors
   Splice variant has been reported.
3. House-Keeping Proteins:
a. p53 suppressor protein
   Splice variant has been reported
b. Heat shock protein hsp 70-House keeping gene.

DETAILED DESCRIPTION OF THE PREFERRED EMBODIMENTS

Figure 1:
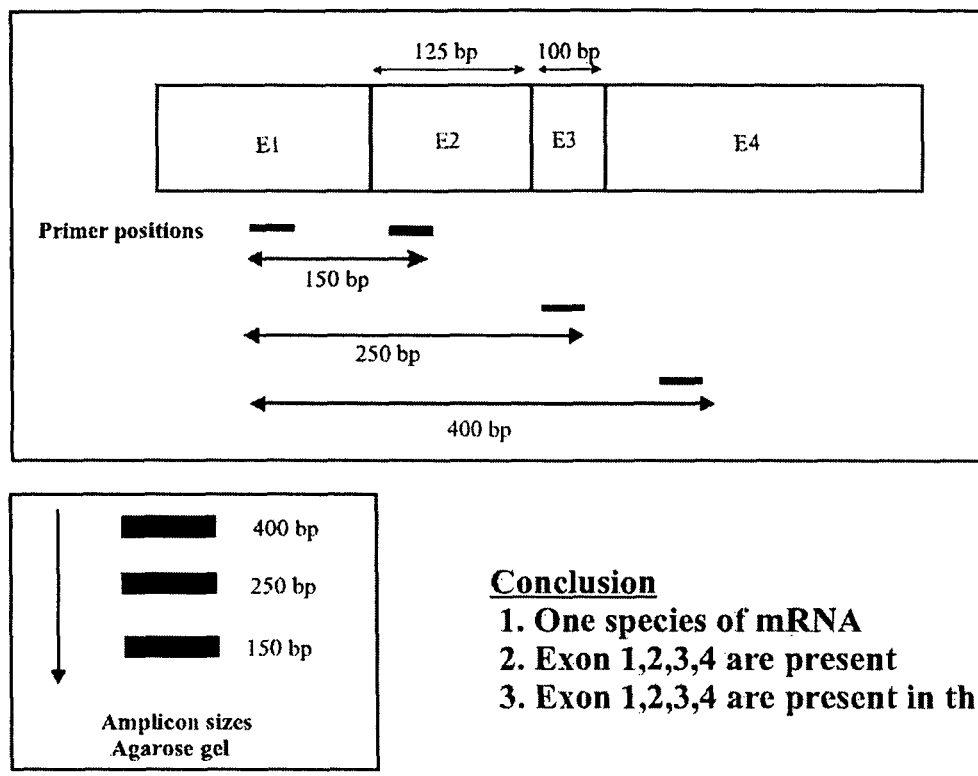
FIGS. 1 to 3 are diagrams illustrating one preferred form of the present invention as it relates to the detection of splice variants.

The present invention may be employed in various situations involving nucleic acid replication, transcription, editing, or other such nucleic acid transformations. However, the invention will first be illustrated as it relates to a situation in which nucleic acid sequences containing two or more specific known (or partially known) nucleic acid sequence units are spliced together or copied during a natural or artificial process and where variations may occur during the splicing or copying procedure. Specifically, the description refers to the translation and editing of genetic DNA containing exons as the specific sequence units, as well as non-coding introns, but it will be appreciated from comments above that this is not the only situation in which the present invention may be employed.

The invention makes use of the polymerase chain reaction (PCR) to amplify short sections of DNA, or reverse transcription PCR (RT-PCR) to amplify complementary DNA (cDNA) from sequences of mRNA (e.g. messenger RNA or mRNA). PCR and RT-PCR are well-known processes that involve well-established techniques described, for example, in Molecular Cloning: A Laboratory Manual, by Sambrook and Russel, 3$^{rd}$ Edition, Cold Spring Harbor Laboratory Press, 2001 (the disclosure of which is incorporated herein by reference). PCR and RT-PCR are very similar, except that reverse transcriptase is used in RT-PCR to initially form cDNA from sample RNA extract, and then the cDNA is subjected to amplification by PCR. In the PCR and RT-PCR procedures, use is made of pairs of primers (upstream, "up" or forward primers, and downstream, "down" or reverse primers), which are short stretches of nucleic acids having sequences designed to anneal to known base sequences of a double-stranded substrate molecule. The primers form the start and stop positions for the sequence replication, so the sequence between (and incorporating) the primers is amplified during the PCR cycles.

In the present invention, primer pairs are designed to cause the amplification of sequences crossing (bracketing) regions of interest where sequence variants may occur. In the context of exon splicing, the regions of interest are the possible junctions between nucleic acid sequence units (exons). Essentially, all possible splice variants (as well as the expected sequence) are worked out in advance so that the expected and possible order in which the exons may be joined is known. Primers are then designed to anneal to parts of the various sequences to reveal (in terms of the amplicons that they produce during PCR) the presence (or absence) of the expected sequence or any variants. This means designing primers that amplify sequences crossing one or more possible splices between exons. The results of PCR or RT-PCR using such primers, e.g. the existence and size of corresponding amplicons, can then be used as information to determine the sequences present in the sample material. Preferably, sufficient primer pairs are designed and provided (either in one PCR procedure, or in several procedures carried out sequentially) to produce amplicons from the expected sequence and all possible splice variants. This can best be illustrated by the following examples in which reference is made to the accompanying drawings.

The bar at the top of FIG. 1 represents an mRNA molecule made up of four exons (RNA sequences) spliced together, i.e. exons E1, E2, E3 and E4. It should be appreciated that, in this example, the number of exons and base pairs shown in the drawing are chosen just for illustration purposes only and that, in real situations, other numbers and lengths may apply. In a simple case, three primer pairs are provided, each having a common upstream primer P1 designed to anneal to a sequence present only in exon E1. Three downstream primers, P2, P3 and P4 are designed to anneal to specific sequences within each of E2, E3 and E4, respectively. When these primers are present during RT-PCR all at the same time, and when the sample mRNA has the exons spliced in the order E1, E2, E3 and E4 as shown, three DNA sequences will be amplified by the RT-PCR procedure. Thus, the primer pair P1:P2 will amplify a 150 base pair (bp) region crossing the E1:E2 splice as shown, primer pair P1:P3 will amplify a 250 bp region crossing the E1:E2 and E2:E3 splices as shown, and primer pair P1:P4 will amplify a 400 bp region crossing the E1:E2, E2:E3 and E3:E4 splices. The presence of these amplicons in the amplification product mixture, and their approximate lengths, can be detected by conventional means, e.g. agarose gel electrophoresis used conventionally to separate amplified DNA products resulting from the PCR procedure. In this case, the electrophoresis will show three bands corresponding to sequences of 150, 250 and 400 bases, as expected (as represented by the lane shown in the lower left hand corner of FIG. 1). This result leads to the conclusion that there is only one specie of mRNA molecule, i.e. that exons E1, E2, E3 and E4 are present, and that the exons are arranged in the expected order.

Figure 2:
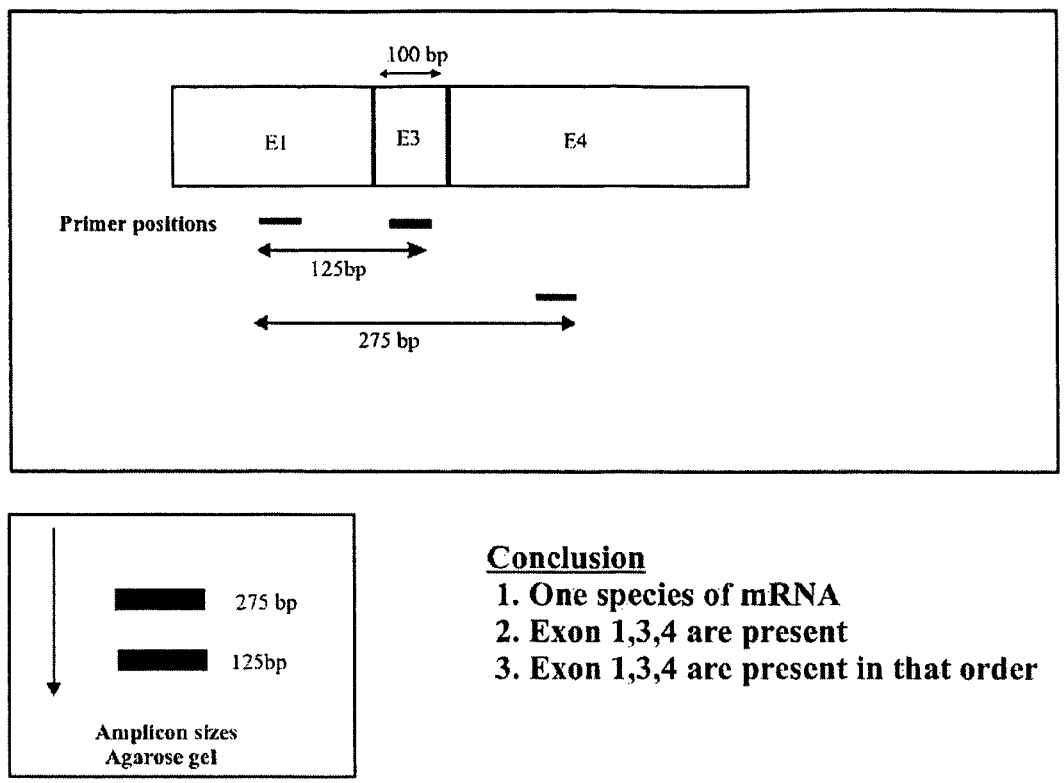

FIG. 2 shows an alternative molecule of mRNA from which exon E2 is absent compared to the sequence of FIG. 1. In this case, downstream primer P2 will not bind to the sample sequence, but downstream primers P3 and P4 will bind as before. However, as E2 has a length of 125 bases (as shown in FIG. 1), but is now absent, the primer pair P1:P3 will now amplify a sequence of 125 bases, and the primer pair P1:P4 will now amplify a sequence of only 275 bases. In such a case, the gel electrophoresis will show two bands corresponding to these amplified sections and the appearance of two such bands will lead to the conclusion that there is only one specie of mRNA present in the sample and that the sample contains exons E1, E3 and E4 arranged in the stated order.

Figure 3:
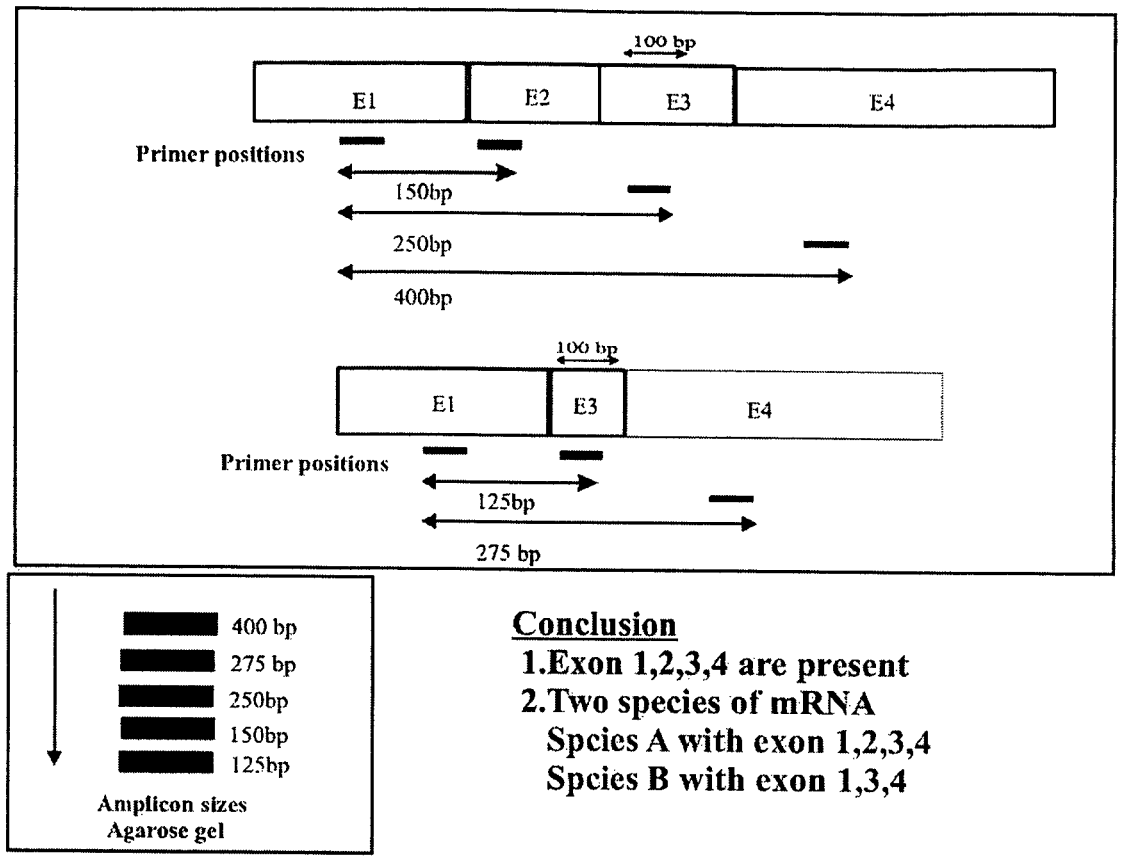

FIG. 3 illustrates a situation in which there are two species of mRNA molecule, i.e. a specie containing E1, E2, E3 and E4 arranged in that order, and a specie consisting only of exons E1, E3 and E4. The first specie will give the results of FIG. 1, i.e. amplification of three sequences of 150, 250 and 400 bp. In the case of the second specie, the result will be the same as in FIG. 2, i.e. the amplification of two sequences of 125 and 275 bp. The combined result will therefore show bands for 5 amplified sequences of 125, 150, 250 275 and 400 bp, as shown in FIG. 3. Therefore, such a result will signify the presence of two variants, one with exons E1, E2, E3 and E4 arranged in the stated order, and the other with only exons E1, E3 and E4 arranged in the stated order.

Therefore, by providing an upstream primer corresponding to a sequence of an exon likely (a) to be in the first position in any variant, and (b) likely to be present in all variants, as well as downstream primers corresponding to a sequences from all other exons likely to be present, the amplification results can be analyzed to determine (1) how many species of mRNA are present, and (2) the number and order of exons in each mRNA variant. The process works for at least three exons and corresponding primers, and may be carried out for any number of exons, provided the resulting sequences can all be amplified by PCR or RT-PCR. Normally, there are 2 to 20 exons present in a functional gene transcript. To avoid ambiguous results, the primers should preferably be designed to produce amplified sequences of different lengths in all cases (the differences of length being sufficient to produce different discernable bands in gel electrophoresis), and the lengths of the exons should be known (as well as at least a part of their sequence so that primers may be designed).

While the above example requires exon E1 to be present in all variants, as well as E1 being the first exon in any likely sequence, if an amplicon is to be obtained, the invention is not limited to such cases. This was necessary only because all of the primers pairs of that example use a common upstream primer P1 that anneals to a section of the sequence of E1. It is possible instead to provide primer pairs having different upstream primers as well as different downstream primers, the primers being designed to amplify sequences that will cross all possible exon-exon splices. Ideally, the upstream primer of each exon is positioned towards the 3'-end of the exon sequence, and the downstream primer is positioned on or close to the 5'-end. For a sequence having six exons E1 to E6 arranged in that order, there would be 15 amplified PCR products, i.e. as shown in Table 1 below:

TABLE 1

| 1 | E1 up | + | E6 down |
| 2 | E1 up | + | E5 down |
| 3 | E1 up | + | E4 down |
| 4 | E1 up | + | E3 down |
| 5 | E1 up | + | E2 down |
| 6 | E2 up | + | E6 down |
| 7 | E2 up | + | E5 down |
| 8 | E2 up | + | E4 down |
| 9 | E2 up | + | E3 down |
| 10 | E3 up | + | E6 down |
| 11 | E3 up | + | E5 down |
| 12 | E3 up | + | E4 down |
| 13 | E4 up | + | E6 down |
| 14 | E4 up | + | E5 down |
| 15 | E5 up | + | E6 down |

These amplicons may be formed in a single PCR reaction using all primer pairs at once, or alternatively, in more than one reaction using different combinations of primer pairs (in the extreme, one primer pair is provided for each PCR reaction). The presence of the stated 15 amplicons indicates that all exons are present and that the order is as expected. However, if (for example) E3 is missing, the amplicons will be as shown in Table 2 below:

TABLE 2

| 1 | E1 up | + | E6 down |
| 2 | E1 up | + | E5 down |
| 3 | E1 up | + | E4 down |
| 4 | E1 up | + | E2 down |
| 5 | E2 up | + | E6 down |
| 6 | E2 up | + | E5 down |
| 7 | E2 up | + | E4 down |
| 8 | E4 up | + | E6 down |
| 9 | E4 up | + | E5 down |
| 10 | E5 up | + | E6 down |

This means that there will be only ten amplicons, and the amplicons that would otherwise have spanned E3 (amplicons 1, 2, 3, 5, 6 and 7) will be reduced in size by number of base pairs in E3. If the number of base pairs in E3 is known, this will indicated that it is E3 that is missing.

On the other hand, if all six exons are present, but the order follows E2, E1, E3, E4, E5 and E6, the following amplicons will be detected, as shown in Table 3 below:

TABLE 3

| 1 | E2 up | + | E6 down |
| 2 | E2 up | + | E5 down |
| 3 | E2 up | + | E4 down |
| 4 | E2 up | + | E3 down |
| 5 | E2 up | + | E2 down |
| 6 | E1 up | + | E6 down |
| 7 | E1 up | + | E5 down |
| 8 | E1 up | + | E4 down |
| 9 | E1 up | + | E3 down |
| 10 | E3 up | + | E6 down |
| 11 | E3 up | + | E5 down |
| 12 | E3 up | + | E4 down |
| 13 | E4 up | + | E6 down |
| 14 | E4 up | + | E5 down |
| 15 | E5 up | + | E6 down |

Thus, there will still be 15 amplicons, but the amplicons involving E1 and E2 will be of a different length than those of the first case above (provided E1 and E2 differ in size and/or binding position of the respective primers). This difference of length will be characteristic of the positioning of the exons in the stated re-arranged order.

An alternative approach uses different primer pairs sequentially. For example, if a primer pair is designed with an upstream primer on E1 and a downstream primer on E6, the following amplicons will be produced if E1 and E6 are present at the ends but the other exons are either present or absent, as shown in Table 4 below:

TABLE 4

| | Full mRNA | | | | | | | |
|---|---|---|---|---|---|---|---|---|
| | E6 | E5 | E4 | E3 | E2 | E1 | | |
| | | | Length (bp) | | | | | |
| | 111 | 143 | 164 | 104 | 200 | 135 | # | Amplicon |
| Exons | | | PCR fragment length | | | | Exons | Size |
| All present | 111 | 143 | 164 | 104 | 200 | 135 | 6 | 857 |
| E5 absent | 111 | | 164 | 104 | 200 | 135 | 5 | 714 |
| E4 absent | 111 | 143 | | 104 | 200 | 135 | 5 | 693 |
| E3 absent | 111 | 143 | 164 | | 200 | 135 | 5 | 753 |
| E2 absent | 111 | 143 | 164 | 104 | | 135 | 5 | 657 |
| E5 & E4 absent | 111 | | | 104 | 200 | 135 | 4 | 550 |
| E5 & E3 absent | 111 | | 164 | | 200 | 135 | 4 | 610 |
| E5 & E2 absent | 111 | | 164 | 104 | | 135 | 4 | 514 |
| E4 & E3 absent | 111 | 143 | | | 200 | 135 | 4 | 589 |
| E4 & E2 absent | 111 | 143 | | 104 | | 135 | 4 | 493 |
| E2 & E3 absent | 111 | 143 | 164 | | | 135 | 4 | 553 |
| E5, E4 & E3 absent | 111 | | | | 200 | 135 | 3 | 446 |
| E5, E4 & E2 absent | 111 | | | 104 | | 135 | 3 | 350 |
| E5, E3 & E2 absent | 111 | | 164 | | | 135 | 3 | 410 |
| E5, E4, E3 & E2 absent | 111 | 143 | | | | 135 | 3 | 389 |
| E5, E4, E3 & E2 absent | 111 | | | | | 135 | 2 | 246 |

The presence or absence of such amplicons indicates the presence or absence of the corresponding exons.

Of course, in this case, if no amplicon whatsoever is produced, it can be assumed that either E1 or E6 (or both) is absent. Further PCR reactions can then be carried out sequentially or simultaneously with primer pairs E1/E5, E2/E6 or E2/E5. A lack of amplicon for one or more of these PCR reactions will show if E1, E6 or both E1 and E6 are missing, e.g. no amplicon from E1/E5 shows that E1 or E5 is missing, no amplicon from E2/E6 shows that E6 or E2 is missing, amplicon produced from E2/E5 confirms that E2 and E5 are present, so the failure to produce an amplicon in one or both of the other reactions means that E1 or E6 is missing.

Figure 4:
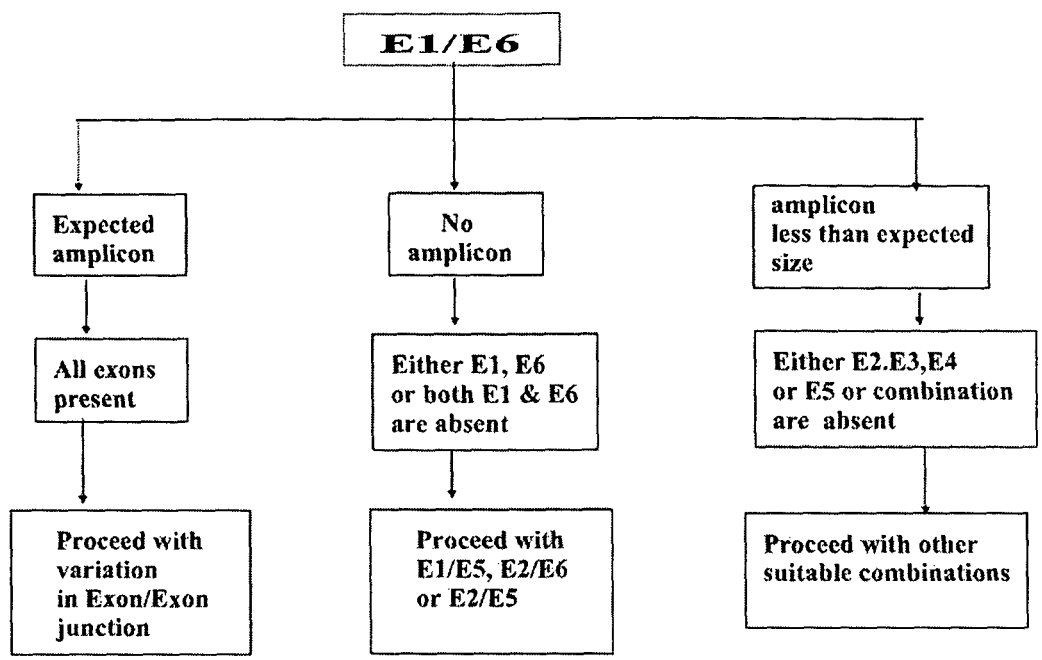
FIG. 4 is a diagram showing a variation of the methods of FIGS. 1 to 3.

This approach can be summarized as shown in FIG. 4 of the accompanying drawings. As represented, an RT-PCR reaction is first carried out with primers E1/E6, and the results will be either an amplicon of the expected size (all exons present in the expected order), in which case the investigation of the precise sequences at the exon-exon junctions may be commenced (see below), or alternatively, no amplicon is produced (which indicates that E1 or E6, or both, are absent and this can be investigated using further RT-PCR with different primer pairs (e.g. E1/E5, E2/E6 and E2/E5 primers), or alternatively, an amplicon of shorter length is detected (which indicates that one of E2, E3, E4 and E5, or a combination of these exons, is missing, in which case further investigation may be carried out with other primer pairs, e.g. E1/E3, etc.).

While the invention is particularly suitable for use with sequences of at least 3 exons, it is possible also to apply it to a sequence of only two exons. In this case, if a single primer pair E1/E2 is employed, an amplicon will either be produced or not. The formation of an amplicon will show that both E1 and E2 are present. The absence of an amplicon will indicate either that E1 or E2 is absent, or that they are reversed (E2: E1). The latter can then be identified by using a primer pair E2/E1.

It should be mentioned that the above procedure may be carried out using the ligase chain reaction as an alternative to PCR and RT-PCR. Ligation is process by which two single stranded nucleotide sequences are joined 3'-prime end to 5'-prime end after both have annealed to a common single-stranded sequence. The joining will only take place across a single nucleotide gap. This may be used to detect the order of exons as well as nucleotide variations across exon/exon junctions.

Figure 5:
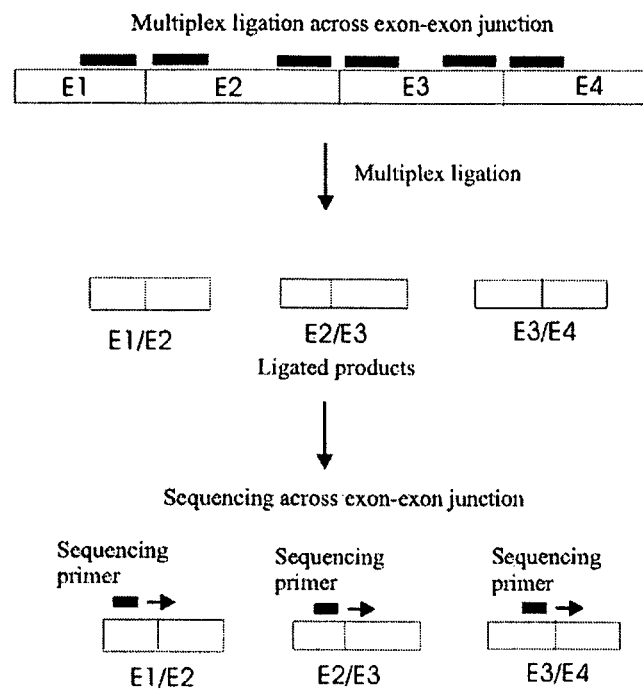
FIG. 5 is a diagram showing an alternative procedure using ligase chain reaction.

The procedure involves designing primers to bracket exon-exon junctions, carrying out conventional multiplex ligation and then sequencing across exon-exon junctions of the resulting amplicons. This is illustrated in FIG. 5 of the accompanying drawings.

Other Sequence Determinations

As noted above, the present invention is particularly suitable for the detection of splice variants, i.e. when known sequence units are spliced together. However, the invention may also be applied to other circumstances, as illustrated in FIG. 6.

Figure 6:
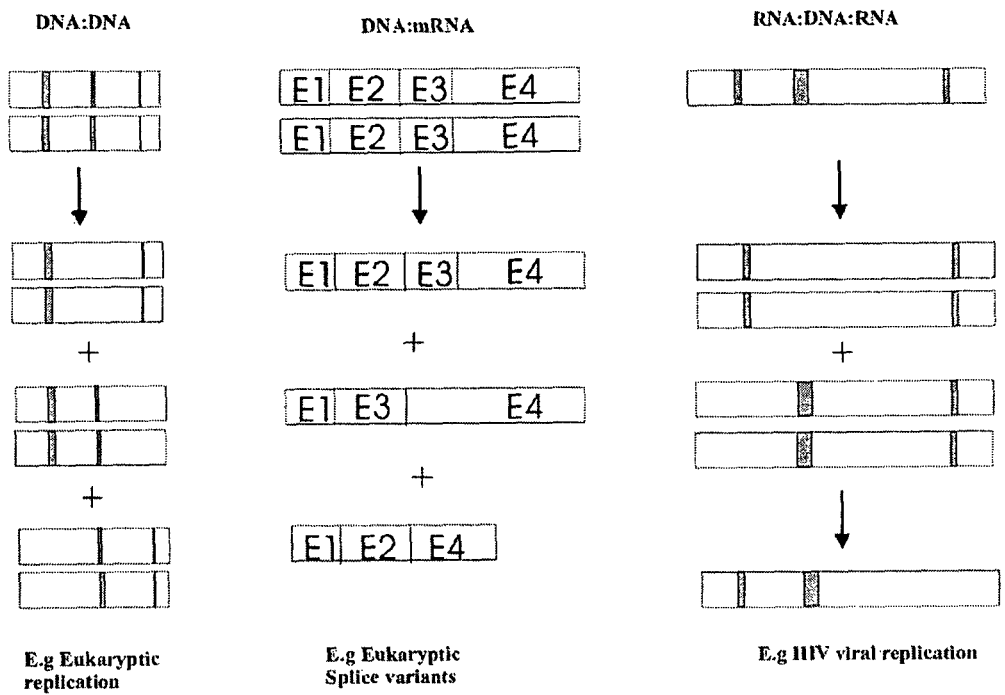
FIG. 6 is a diagram showing alternative transformations to which the present invention may be applied.

In FIG. 6, the left hand column illustrates DNA to DNA replication that takes place, for example, during the processes of eukaryotic cells. The box pair at the top represent DNA containing three "markers" shown in grey (i.e. sequences of interest to a researcher, such as sequences that may indicate a genetic disease, a single nucleotide polymorphism—SNP, or a possible binding site for a drug, or a modification that affects protein folding). During replication, as well as an expected sequence containing all three markers positioned identically to the substrate DNA, there are possible variants, e.g. as shown in the three box pairs beneath the arrow (which represents replication). In the three variants shown, one of the three markers is missing, but a different one in each case. There could, of course, be additional variants with two or all of the markers missing, but this may be statistically less-likely. In such a case, the present invention may be operated by designing primers to amplify sequences crossing the markers and analyzing the resulting amplicons by sequencing. Hence, the amplicons reveal the variants present.

The central column of FIG. 6 illustrates the splicing of exons as already described in detail above.

The right hand column in FIG. 6 illustrates conversion of RNA to DNA and then further conversion of DNA to RNA. Such conversions are typical of RNA viral replication in cells, e.g. the HIV virus. As illustrated, the viral RNA may contain three markers of interest. This RNA is converted to DNA as shown by the arrow but, in addition to the expected sequence containing all three markers, two variants are shown each having one of the markers missing. When the DNA is inserted into the genome of a host and the DNA is transcribed to RNA, the RNA may lack the third marker as shown. The presence or absence of the markers in the final RNA may be determined by carrying out RT-PCR using primers designed to bracket each of the marker sequences, as in the case described for the left hand column. The resulting amplicons can thus reveal the presence or absence of the marker sequences of interest.

It will therefore be seen that the present invention, in one broad form, applies when a nucleic acid transformation takes place from a sequence containing two or more sequences or sequence units of interest and the transformation may result in the formation of variants that lack one of more of the sequences or sequence units of interest or contain such sequences or sequence units in re-arranged order. By designing primers targeted to produce amplicons that reveal the presence of such sequences or sequence units, or such differences in order thereof, the presence (or absence) of the expected sequence or one or more variants may be revealed.

Detection of Variants that Differ By a Small Number of Bases

The above procedure identifies missing or mis-arranged sequences of interest, e.g. exons, but it may not be sufficiently precise to reveal variants that differ by only a few base pairs, e.g. minor deletions at exon-exon junctions, because gel electrophoresis designed for separation of molecules of significant size differences may not discernibly separate molecules that differ only by a few bases (e.g. 1 to 25 bases). If such sequence variations are of interest (which is often the case, because such variations also affect protein folding when translated), a further process of the invention may be employed to determine the formation of such variants. This method is preferably carried out after the above procedure, i.e. after the presence of variants incorporating larger sequences segments of interest, have been determined.

Using the splicing of exons as an example, essentially, in this method, a section of an amplicon extending across an exon-exon junction of interest is isolated and then subjected to cycle sequencing to establish the exact sequence of bases in the region of the junction. However, since cycle sequencing may be carried out on only short sequences, the method involves isolating for such sequencing a short section including the part where small variations may occur (e.g. at the exon-exon junctions).

Cycle sequencing is a known procedure that is employed to determine the exact sequence of bases within a short stretch of DNA (see for example, Hisashi Yamakawa and Osamu Ohara, "A DNA Cycle Sequencing Reaction that Minimizes Compressions on Automated Fluorescent Sequencers", Nucleic Acid Research, Vol. 25, No. 6, pp. 1131-1312, the disclosure of which is incorporated herein by reference). In chain terminator sequencing (Sanger sequencing), extension is initiated at a specific site on the template DNA by using a short oligonucleotide 'primer' complementary to the template at that region. The oligonucleotide primer is extended using a DNA polymerase, an enzyme that replicates DNA. Included with the primer and DNA polymerase are the four deoxynucleotide bases (DNA building blocks), along with a low concentration of a chain terminating nucleotide (most commonly a di-deoxynucleotide). Limited incorporation of the chain terminating nucleotide by the DNA polymerase results in a series of related DNA fragments that are terminated only at positions where that particular nucleotide is used. The fragments are then size-separated by electrophoresis in a slab polyacrylamide gel, or more commonly, in a narrow glass tube (capillary) filled with a viscous polymer (Pop 7; Applied Biosystems, USA). Each sample has a primer of the four normal deoxynucleotides (dATP, dGTP, dCTP and dTTP), DNA polymerase, and all four of the dideoxynucleotides (ddATP, ddGTP, ddCTP and ddTTP) added to it in the same tube. The dideoxynucleotides are added in limited quantities. The primer or the dideoxynucleotides has a fluorescent tag. As the DNA strand is elongated the DNA polymerase catalyses the joining of deoxynucleotides to the corresponding bases. However, if a di-deoxynucleotide is joined to a base, then that fragment of DNA can no longer be elongated since a dideoxynucleotide lacks a crucial 3'-OH group. Fragments of all sizes should be obtained due to the randomness of when a dideoxynucleotide is added. However, to make sure that all different lengths will occur, only short stretches (less than about 800 bases) of DNA can be sequenced in one test. The DNA is then denatured and the resulting fragments are separated (with a resolution of just one nucleotide) by gel electrophoresis, from longest to shortest. Amplicons were sequenced by cycle sequencing using ABI PRISM Big Dye Terminator Cycle Sequencing Ready Reaction Kit (Applied Biosystems, USA) on a GeneAmp 2400 thermocycler (PE Applied Biosystems, USA) using thermocycler. Unincorporated dye terminators were removed using Centricep chromatography columns (Princeton, USA). The samples were then dried, and re-suspended in 20 ul of ABI PRISM Template Suppression Reagent (TSR). Samples were analyzed by capillary electrophoresis using the ABI PRISM Genetic Analyzer 310. The 47 cm×50 um uncoated capillary was filled with a Performance Optimized Polymer 6 (acrylamide/urea polymer) and heated to 500 C. 20 ul of the sequencing mixture was pipetted into a 0.2 mL microfuge tube provided by the manufacturer (Applied Biosystems, USA). Samples were drawn into the capillary by electrokinetic injection at 2 Kv for 50 to 200 seconds. The electrophoresis was carried out at 15 Kv for 20 minutes Preferred cycle sequencing procedures are illustrated in the following with reference to FIGS. 5, 7 and 8.

Figure 7:
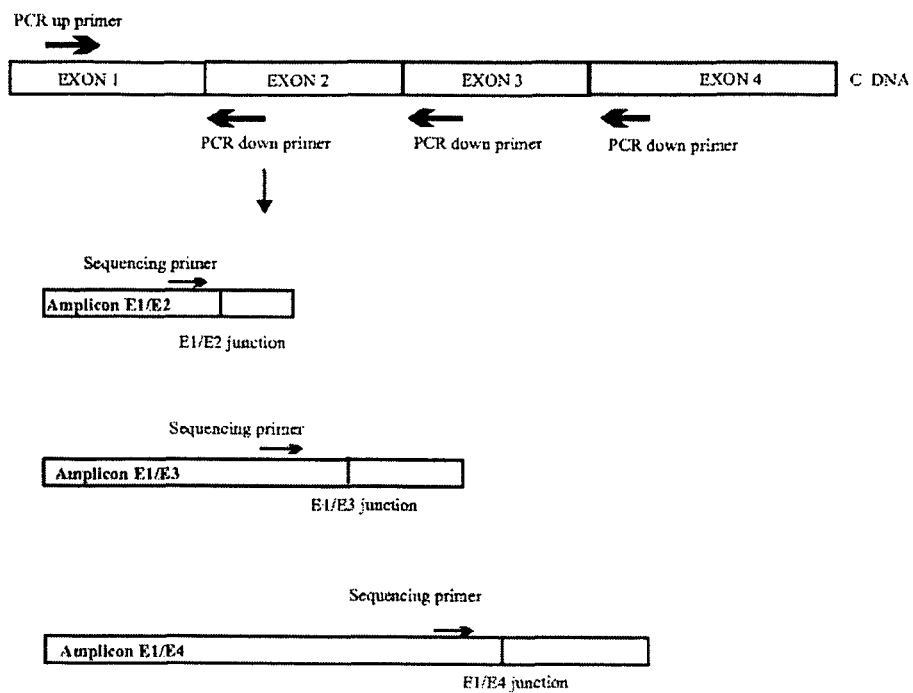
FIGS. 7 and 8 are diagrams illustrating other preferred forms of the invention as it relates to the determination of precise sequences at the junctions of adjacent nucleic acid sequence units.

FIG. 7 represents a procedure similar to that of FIG. 1 using PCR downstream primers that anneal close to or at the exon junctions E1:E2, E2:E3, E3:E4, which thereby produce amplicons having 3'-ends spanning and terminating close to the junctions. The resulting amplicons (after being used confirming the presence of the exons and the order of alignment) can be used for cycle sequencing.

Figure 8:
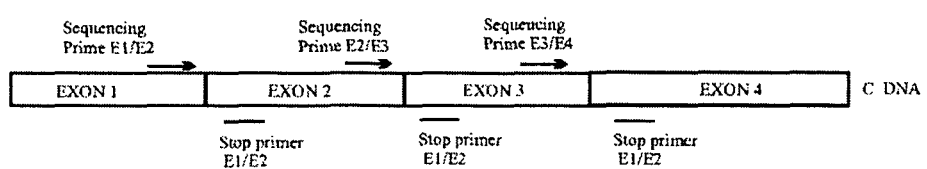

FIG. 8 shows the use of stop primers designed to terminate sequencing at a position more than a few bases on the downstream sides of the junctions of several exons on an amplicon that spans several exons. Sequencing primers designed to anneal just a few bases upstream of the junctions are also used for sequencing.

Essentially, one of three methods may be employed.

(1) Assuming that a peptide nucleic acid (PNA) stop primer method can be implemented, the following steps may be carried out.

(i) PNA primers are designed that will bind to each exon approximately 10 to 15 base pairs on the 3' side of the exon-exon junction.

(ii) The sample DNA is denatured and PNA primers added, and they are allowed to anneal to the sample DNA.

(iii) A dye terminator is added (e.g. Big Dye Terminator® v3.1 of Applied Biosystem, USA), sequencing primers are added and cycle sequence performed.

(iv) Sequencing is carried out preferably on a capillary gel sequencer or a flat gel electrophoresis to establish the exact sequence of the isolated DNA section.

PNA is an artificially synthesized chemical similar to DNA or RNA but differing in the composition of its "backbone" which comprises repeating N-(2-aminoethyl)-glycine units linked by peptide bonds. The various purine and pyrimidine bases are linked to the backbone by methylene carbonyl bonds. Since the backbone of PNA contains no charged phosphate groups, the binding between PNA/DNA strands is stronger than between DNA/DNA strands due to the lack of electrostatic repulsion. PNA thus stops further DNA replication during PCR and hence can be used to tailor amplicons to match regions of interest.

(2) Assuming Stoffel conditions (PCR without 5'-3' exonuclease activity) and that stop primers work.
  (i) Design stop primers that will bind to each exon approximately 10-15 bp on the 3' side of the junction.
  (ii) Create single-stranded DNA (ssDNA) using PCR technology and only one primer.
  (iii) Add the stop primers and allow them to anneal.
  (iv) Add the dye terminator mixture (e.g. BDT v3.1; Applied Biosystems, USA) and the sequencing primers and sequenced in a thermocycler.

Stoffel conditions allow the use of the so-called "Stoffel fragment" for PCR. This is a modified form of AmpliTaq® DNA polymerase from which the N-terminal 289 amino acids have been deleted. The Stoffel fragment differs from AmpliTaq® DNA polymerase in that it is more thermostable (by approximately two-fold), exhibits optimal activity over a broader range of magnesium ion concentration (2 mM-10 mM) and lacks intrinsic 5' to 3' exonuclease activity. The unique properties of the Stoffel fragment make it especially useful for arbitrarily primed PCR (AP-PCR) or random amplified polymorphic DNA (RAPD) amplification methods, whereby genomic DNA is amplified with a set of short primers of arbitrary sequence.

(3) Carry out a series of PCRs to generate short amplicons from the entire gene sequence, e.g. exons 1-2, 2-3, 3-4 and 4-5 (in individual tubes)
  (i) Design primers that are 15-20 bp on the 5' side of the 3' end of the downstream primer for each exon.
  (ii) The amplicons are then pooled for 1 cycle sequencing reaction.

The presence or absence of a sequence (expected sequence or variant sequence) will indicate which primer sets are required for additional PCR reactions and cycle sequencing steps.

1. Digest the fragments with restriction enzymes so that every exon is cleaved into two pieces.
2. A sequencing primer can then be used to sequence each exon-exon junction to determine which exon is absent or nucleotide variation at the splicing junction.

The invention is illustrated in further detail by reference to the following Examples which are not intended to limit the scope of the present invention.

Example 1

Summary

Three gene expressions were analyzed, namely: prostrate specific membrane antigen (PSMA) in PC3 cell lines, tumor suppressor protein (p53) and (HTT) in SW480 and hepatoma cell lines. It was found that PSMA had one splice variant, PSMAV1, lacking exon 19. However, PSMAV1 exhibited nucleotide sequence variations at the exon18/exon20 junction. There were no splice variants observed for p53 tumor suppressor gene in these three cell lines. However, gene expression in SW480 and hepatoma cells had nucleotide variations between the exon8/exon9 junctions.

Materials and Methods
Cell Cultures

Cell cultures of Vero E6 cells were obtained from the University of Saskatchewan. These cells were grown in RPMI medium supplemented with 5% fetal calf serum in a 50 ml culture.

Total RNA Extraction

Total RNA was extracted using the RNeasy® Mini Kit (Qiagen, USA). The reagents of the kit were prepared according to the manufacturer's instructions and 350 μL of RLT buffer and 250 μL of 100% ethanol were added to 100 μL of viral lysate. The sample was transferred to a spin column and centrifuged at 8,000 rcf for 30 seconds. The sample was washed on the spin column three times, once with 700 μL RW1 buffer and twice with 500 μL RPE buffer. After each wash the spin column was centrifuged at 8,000 rcf for 30 seconds. After washing, the column was thoroughly dried with a 1-minute centrifugation at 8,000 rcf. Finally, the sample was eluted from the column by adding 50 μL RNase-free water to the column and centrifuging for 1 minute at 8,000 rcf. The RNA was further concentrated by re-applying the eluate to the column and centrifuging a second time at 8,000 rcf for 1 minute.

RT-PCR

The SuperScript® One-Step RT-PCR with Platinum Taq kit (Invitrogen, USA) was used for individual RT-PCR. The reaction volume was 50 μL which consisted of 25 μL 2× Reaction mix, 200 nM of each primer, 1 μL RT/Platinum mix Taq and 50 ng of West Nile Virus RNA. The tubes were placed in a thermocycler, GeneAmp® 2400 (Applied Biosystems, USA) and amplified according to the thermocycling profile shown in Table 1.

Gel Electrophoresis

The amplicons were visualized by loading 2 μL 6× loading buffer, 5 μL TBE buffer and 5 μL of the PCR product onto a 2% agarose gel and applying 110V for 50 minutes. The gel was then stained for 15 minutes in ethidium bromide (5 μg/ml) TBE solution and then destained in distilled water for 15 minutes.

Cycle Sequencing

Amplicons were sequenced by cycle sequencing using ABI PRISM Big Dye Terminator® Cycle Sequencing Ready Reaction Kit (Applied Biosystems, USA) on a GeneAmp 2400 thermocycler (PE Applied Biosystems, USA) using thermocycler profile on Table 1. Unincorporated dye terminators were removed using Centricep® chromatography columns (Princeton, USA). The samples were then dried, and re-suspended in 20 μl of ABI PRISM Template Suppression Reagent. Samples were analyzed by capillary electrophoresis using the ABI PRISM Genetic Analyzer 310. The 47 cm×50 um uncoated capillary was filled with a Performance Optimized Polymer® 6 (acrylamide/urea polymer) and heated to 50° C. 20 μl of the sequencing mixture was pipetted into a 0.2 mL microfuge tube provided by the manufacturer (Applied Biosystems, USA). Samples were drawn into the capillary by an electric current (electrokinetic injection) at 2 Kv for 50 to 200 seconds. The electrophoresis was carried out at 15 Kv for 20 minutes.

Results

Total RNA was extracted from PC3 prostate cancer cell lines, SW480, HTT29 and human hepatoma cancer cells.

P53

RT-PCR with exon 1 up-primer and exon 6 down-primer produced expected band 677 bp. RT-PCR with exon 6 up-primer and exon 11 down-primer produced expected band 542 bp.

HTT

RT-PCR with HTT 1a and HTT 1b produced expected band 562 bp; HTT 2a and HTT 2b produced expected band 513 bp, HTT 3a and HTT 3b produced expected band 706 bp.

PSMA

RT-PCR with Exon4 up/exon 8 down produced expected band of 569 bp and Exon 17 up/exon 20 down produced expected band 441 bp and abnormal band of 341 bp. Sequencing whole amplicon (341 bp) confirmed that exon 19 is missing.

Based on the amplicon sizes it generated, PSMA showed two transcripts; a full length mRNA and an alternative splice variant without exon19; both p53 and HTT had only one transcript each. These amplicons were sequenced using upstream PCR primer. Transcript from PSMA showed nucleotide variations at exon18/exon20 junction to that of the reported results. Similarly, p53 showed nucleotide variations at exon8/exon9 junction.

The primers used in this Example are shown in Table 5 below:

TABLE 5

| | Primers | |
|---|---|---|
| P53 | | |
| P53 | 1exonup:466u18 | GGGACACTTTGGTTCGGG (SEQ ID NO. 1) |
| P53 | down34exon:654L16 | TGGGACGGCAAGGGGG (SEQ ID NO. 2) |
| P53 | down5exon:935L20 | ATCTTGTTGAGGGCAGGGGA (SEQ ID NO. 3) |
| P53 | down6exon:112L21 | GGATAAGATGCTGAGGAGGGG (SEQ ID NO. 4) |
| P53 | 6exonup:1157U21 | TTGCGTGTGGAGTATTTGGAT (SEQ ID NO. 5) |
| P53 | down11exon:1678L21 | TTATGGCGGGAGGTAGACTGA (SEQ ID NO. 6) |
| HTT | | |
| HTT | Htt1a:130U21 | ATTCTCAGAAGCAGCTATCAG (SEQ ID NO. 7) |
| HTT | Htt1b:635L21 | CAGGCCATGATGGTGTTGTAG (SEQ ID NO. 8) |
| HTT | Htt2a:738U21 | ACCAATTACTTCTCCGAGGAC (SEQ ID NO. 9) |
| HTT | Htt2b:1230L21 | GAAGATGACAAATCCCGAAAC (SEQ ID NO. 10) |

TABLE 5-continued

| | Primers | |
|---|---|---|
| HTT | Htt3a:1981L21 | ACACAGCATTCAAGCGGATGT (SEQ ID NO. 11) |
| HTT | Htt3b:1296U18 | GAGGTGGCCAAAGACGCA (SEQ ID NO. 12) |
| PSMa | | |
| PSM | e4psm:608U25 | TGTTGTCCTACCCAAATAAGACTCA (SEQ ID NO. 13) |
| PSM | e8psm:1152L25 | GAGCTTCTGTGCATCATAGTATCCA (SEQ ID NO. 14) |
| PSM | e17psm:2114U26 | ATCCACAGGAAATGAAGACATACAGT (SEQ ID NO. 15) |
| PSM | e20psm:2528L27 | ATACCACACAAATTCAATACGGATTCT (SEQ ID NO. 16) |

REFERENCES

1) Molecular Biology of the Cell, by Bruce Alberts et al, 1994 Garland Science publication).
2) Kotera J, Fujishige K, Michibata H, Yuasa K, Kubo A, Nakamura Y, Omori K., Biochem. Pharmacol. 2000 Nov. 1;60(9): 1331-41, Characterization and effects of methyl-2-(4-aminophenyl)-1,2-dihydro-1-oxo-7-(2-pyridinylmethoxy)-4-(3,4,5-trimethoxyphenyl)-3-isoquinoline carboxylate sulfate (T-1032), a novel potent inhibitor of cGMP-binding cGMP-specific phosphodiesterase (PDE5).
3) Schmittgen T D, Teske S, Vessella R L, True L D, Zakrajsek B A., Int J Cancer. 2003 Nov. 1; 107(2):323-9, *Expression of prostate specific membrane antigen and three alternatively spliced variants of PSMA in prostate cancer patients.*
4) Martin M M, Willardson B M, Burton G F, White C R, McLaughlin J N, Bray S M, Ogilvie J W Jr, Elton T S., Mol. Endocrinol. 2001 February: 15(2):281-93, *Human angiotensin II type I receptor isoforms encoded by messenger RNA splice variants are functionally distinct.*
5) He X, Ee P L, Coon J S, Beck W T., Clin. Cancer Research. 2004 Jul. 15:10(14):4652-60, *Alternative splicing of the multidrug resistance protein 1/ATP binding cassette transporter subfamily gene in ovarian cancer creates functional splice variants and is associated with increased expression of the splicing factors PTB and SRp20.*
6) Wistow G, Bernstein S L, Wyatt M K, Ray S, Behal A, Touchman J W, Bouffard G, Smith D, Peterson K., Mol. Vis 2002 Jun. 15:8:196-204, *Expressed sequence tag analysis of human retina for the NEIBank Project: retbindin, an abundant, novel retinal cDNA and alternative splicing of other retina-preferred gene transcripts.*

The invention claimed is:

1. A method for determining the presence or absence, in a sample, of an expected splicing arrangement of a gene or a method of determining the presence or absence in a sample of one or more variant splicing arrangement of the gene, the method comprising:
provided in a sample of mRNA and/or cDNA, wherein the mRNA and/or cDNA comprises an expected splicing arrangement of the exons of the gene and/or one or more variant splicing arrangements of the exons of the gene, wherein the mRNA and/or cDNA comprises from three to six joined exons in said expected splicing arrangement and/or one or more variant splicing arrangement, wherein the size of each of the three to six joined exons is less than 1 kb, a forward primer designed to be capable of hybridizing to one exon of the three to six joined exons and a plurality of reverse primers, wherein each reverse primer is designed to be capable of hybridizing to another exon of the three to six joined exons, wherein the forward and reverse primers are capable of generating an amplicon or amplicons comprising one or more exon:exon junction,
incubating the sample and primers in a single reaction vessel under conditions sufficient to generate an amplicon or amplicons;
assessing the amplicon or amplicons so generated,
thereby determining the presence or absence of one or more expected splicing arrangement of a gene and of one or more variant splicing arrangements based on the number of amplicon or amplicons generated and/or the size or sizes of one or more of the amplicon or amplicons.

2. The method of claim 1, wherein said assessing is carried out by gel electrophoresis.

3. The method of claim 1, wherein the amplicon or amplicons comprises the expected splicing arrangement of the gene and one or more variant splicing arrangement of the gene.

4. The method of claim 3, wherein the method detects the presence of the expected splicing arrangement of the gene and one or more variant splicing arrangement of the gene.

5. A method of determining sequence identity, the method comprising:
performing the method of claim 1; and
determining a nucleotide sequence of a region of at least one of the amplicon or amplicons comprising at least one of the exon:exon junctions.

6. A method of determining sequence identity, the method comprising:
performing the method of claim 1; and
determining a nucleotide sequence of a plurality of regions of a nucleic acid present in the sample, each region respectively comprising one of the exon:exon junctions of the expected splicing arrangement or of a variant splicing arrangement of the gene.

* * * * *

SEQUENCE LISTING

<160> NUMBER OF SEQ ID NOS: 16

<210> SEQ ID NO 1
<211> LENGTH: 18
<212> TYPE: DNA
<213> ORGANISM: Artificial Sequence
<220> FEATURE:
<223> OTHER INFORMATION: Synthetic primer

<400> SEQUENCE: 1

-continued gggacactttggttcggg                                      18

<210> SEQ ID NO 2
<211> LENGTH: 16
<212> TYPE: DNA
<213> ORGANISM: Artificial Sequence
<220> FEATURE:
<223> OTHER INFORMATION: Synthetic primer

<400> SEQUENCE: 2 tgggacggcaaggggg                                        16

<210> SEQ ID NO 3
<211> LENGTH: 20
<212> TYPE: DNA
<213> ORGANISM: Artificial Sequence
<220> FEATURE:
<223> OTHER INFORMATION: synthetic primer

<400> SEQUENCE: 3 atcttgttgagggcagggga                                    20

<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4 ggataagatgctgaggagggg                                   21

<210> SEQ ID NO 5
<211> LENGTH: 21
<212> TYPE: DNA
<213> ORGANISM: Artificial Sequence
<220> FEATURE:
<223> OTHER INFORMATION: synthetic primer

<400> SEQUENCE: 5 ttgcgtgtggagtatttggat                                   21

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6 ttatggcgggaggtagactga                                   21

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7 attctcagaagcagctatcag                                   21

<210> SEQ ID NO 8
<211> LENGTH: 21
<212> TYPE: DNA

```
<213> ORGANISM: Artificial Sequence
<220> FEATURE:
<223> OTHER INFORMATION: Synthetic primer

<400> SEQUENCE: 8
caggccatga tggtgttgta g                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
accaattact tctccgagga c                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic primer

<400> SEQUENCE: 10
gaagatgaca aatcccgaaa c                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11
acacagcatt caagcggatg t                                              21

<210> SEQ ID NO 12
<211> LENGTH: 18
<212> TYPE: DNA
<213> ORGANISM: Artificial Sequence
<220> FEATURE:
<223> OTHER INFORMATION: Synthetic primer

<400> SEQUENCE: 12
gaggtggcca aagacgca                                                  18

<210> SEQ ID NO 13
<211> LENGTH: 25
<212> TYPE: DNA
<213> ORGANISM: Artificial Sequence
<220> FEATURE:
<223> OTHER INFORMATION: Synthetic Primer

<400> SEQUENCE: 13
tgttgtccta cccaaataag actca                                          25

<210> SEQ ID NO 14
<211> LENGTH: 25
<212> TYPE: DNA
<213> ORGANISM: Artificial Sequence
<220> FEATURE:
<223> OTHER INFORMATION: Synthetic Primer

<400> SEQUENCE: 14
gagcttctgt gcatcatagt atcca                                          25
```

```
<210> SEQ ID NO 15
<211> LENGTH: 26
<212> TYPE: DNA
<213> ORGANISM: Artificial Sequence
<220> FEATURE:
<223> OTHER INFORMATION: Synthetic Primer

<400> SEQUENCE: 15
atccacagga aatgaagaca tacagt                                          26

<210> SEQ ID NO 16
<211> LENGTH: 27
<212> TYPE: DNA
<213> ORGANISM: Artificial Sequence
<220> FEATURE:
<223> OTHER INFORMATION: Synthetic Primer

<400> SEQUENCE: 16
ataccacaca aattcaatac ggattct                                         27
```